(12) United States Patent
Akagane

(10) Patent No.: US 9,427,248 B2
(45) Date of Patent: Aug. 30, 2016

(54) ULTRASONIC PROBE

(71) Applicant: OLYMPUS CORPORATION, Hachioji-Shi, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 173 days.

(21) Appl. No.: 13/673,532

(22) Filed: Nov. 9, 2012

(65) Prior Publication Data

US 2013/0131705 A1 May 23, 2013

Related U.S. Application Data

(63) Continuation of application No. PCT/JP2012/054802, filed on Feb. 27, 2012.

(60) Provisional application No. 61/447,938, filed on Mar. 1, 2011.

(51) Int. Cl.
*A61B 17/32* (2006.01)
*A61N 7/00* (2006.01)
(Continued)

(52) U.S. Cl.
CPC ............ *A61B 17/320068* (2013.01); *A61B 17/320092* (2013.01); *A61N 7/00* (2013.01); *A61B 18/1445* (2013.01); *A61B 2017/00526* (2013.01); *A61B 2017/22015* (2013.01); *A61B 2018/00428* (2013.01); *A61B 2018/00589* (2013.01); *A61B 2018/00994* (2013.01); *A61B 2217/005* (2013.01)

(58) Field of Classification Search
CPC ............. A61B 17/320068; A61B 17/320092; A61B 2017/22015; A61B 2217/005; A61B 18/1445; A61N 7/00
USPC ....................... 606/169, 39, 40, 22
See application file for complete search history.

(56) References Cited

U.S. PATENT DOCUMENTS 3,433,226 A * 3/1969 Boyd ........................ 606/159
4,750,488 A * 6/1988 Wuchinich et al. ......... 606/128
(Continued)

FOREIGN PATENT DOCUMENTS

CN 1756512 A 4/2006
JP A-04-212338 8/1992
(Continued)

OTHER PUBLICATIONS

Mar. 19, 2012 International Preliminary Report on Patentability issued in International Application No. PCT/JP2012/054802 (w/ English Translation).
(Continued)

*Primary Examiner* — Corrine McDermott
*Assistant Examiner* — Sarah Simpson
(74) *Attorney, Agent, or Firm* — Oliff PLC

(57) ABSTRACT

An ultrasonic probe includes a probe body which includes an outer peripheral portion provided along a longitudinal axis, and a void defining surface defining a void, which is open to an outside along the longitudinal axis in at least one part of the outer peripheral portion, along the longitudinal axis. The void defining surface defines the void in the probe body from a first anti-node position of the ultrasonic vibrations to a second anti-node position of the ultrasonic vibrations different from the first anti-node position.

8 Claims, 13 Drawing Sheets

(51) Int. Cl.
*A61B 18/14* (2006.01)
*A61B 18/00* (2006.01)
*A61B 17/00* (2006.01)
*A61B 17/22* (2006.01)

(56) References Cited

U.S. PATENT DOCUMENTS

| | | | |
|---|---|---|---|
| 5,163,433 A * | 11/1992 | Kagawa et al. | 601/2 |
| 5,595,328 A | 1/1997 | Safabakhsh et al. | |
| 5,688,235 A | 11/1997 | Sakurai et al. | |
| 6,875,220 B2 * | 4/2005 | Du et al. | 606/169 |
| 2002/0077550 A1 | 6/2002 | Rabiner et al. | |
| 2004/0158150 A1 | 8/2004 | Rabiner et al. | |

FOREIGN PATENT DOCUMENTS

| | | |
|---|---|---|
| JP | A-2001-161705 | 6/2001 |
| JP | A-2005-027809 | 2/2005 |
| WO | WO 99/44514 | 9/1999 |

OTHER PUBLICATIONS

International Search Report issued in International Application No. PCT/JP2012/054802 dated Mar. 19, 2012 (with translation).
Feb. 24, 2014 Extended European Search Report issued in European Patent Application No. EP 12 75 2458.
Sep. 25, 2015 Search Report issued in European Application No. 12752458.5.
Mar. 2, 2015 Office Action issued in Chinese Application No. 201280005786.5.

* cited by examiner

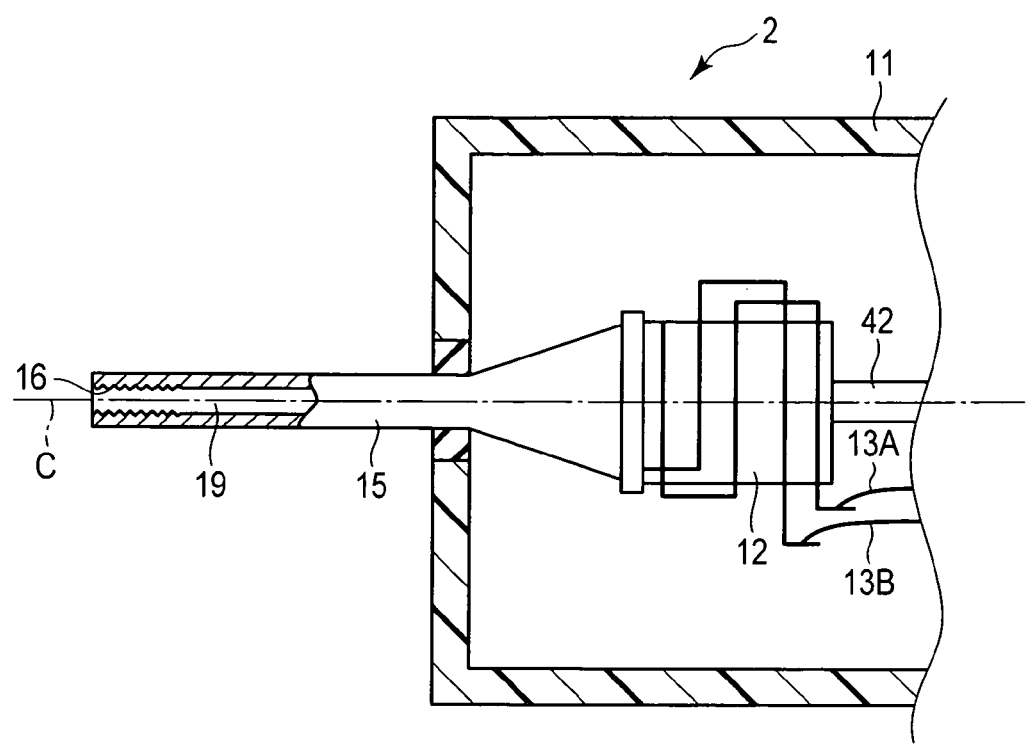
F I G. 2

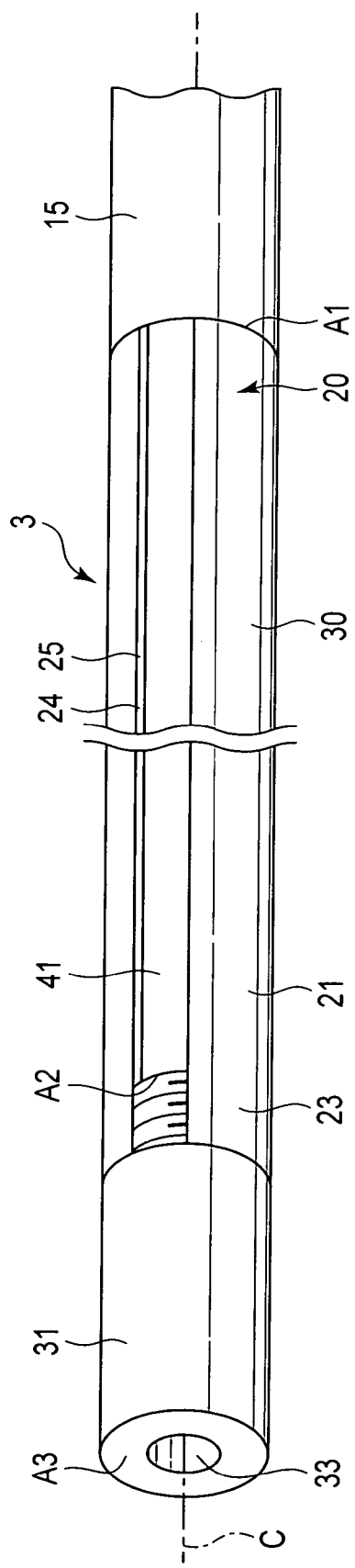
F I G. 3

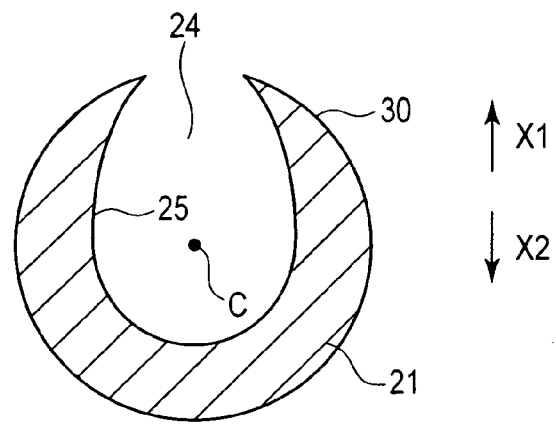
F I G. 5
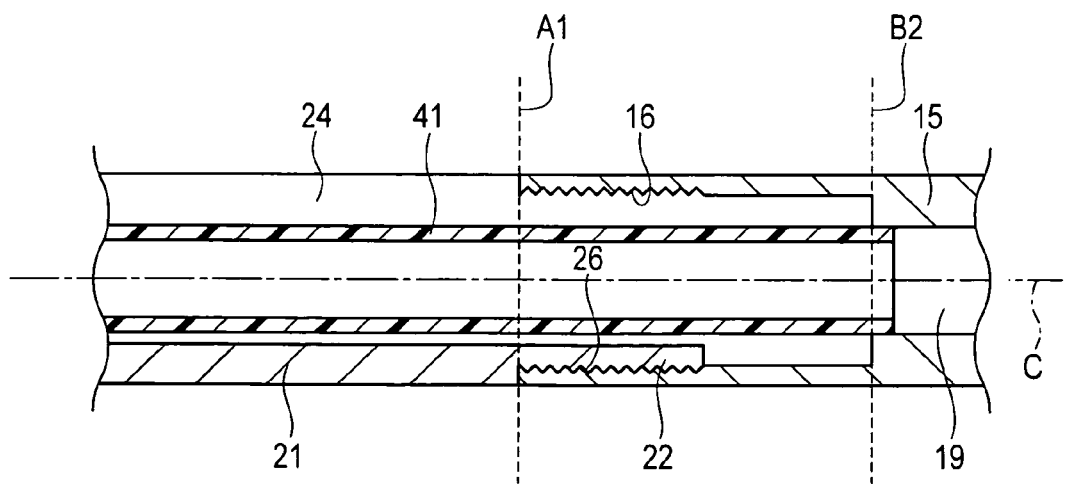
F I G. 6

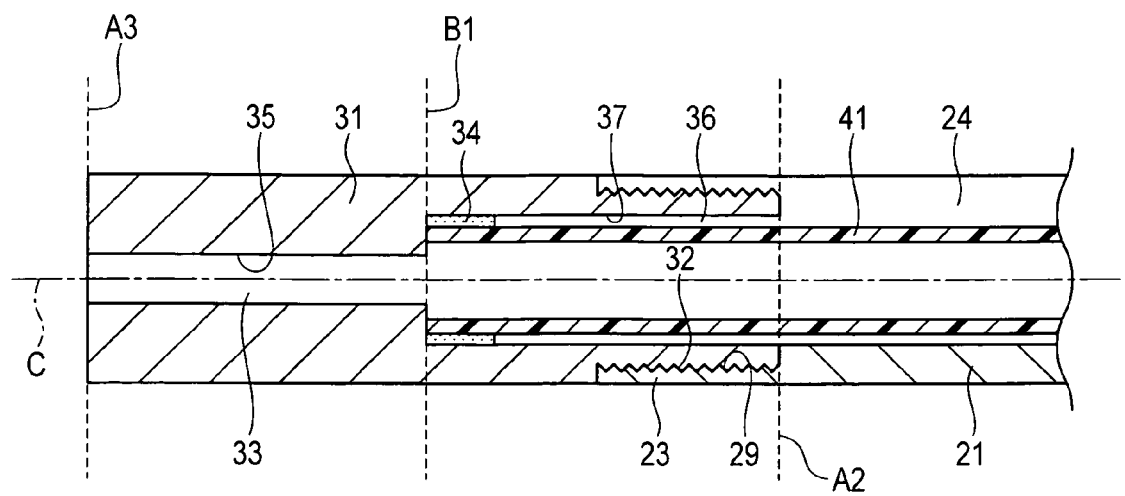
F I G. 7
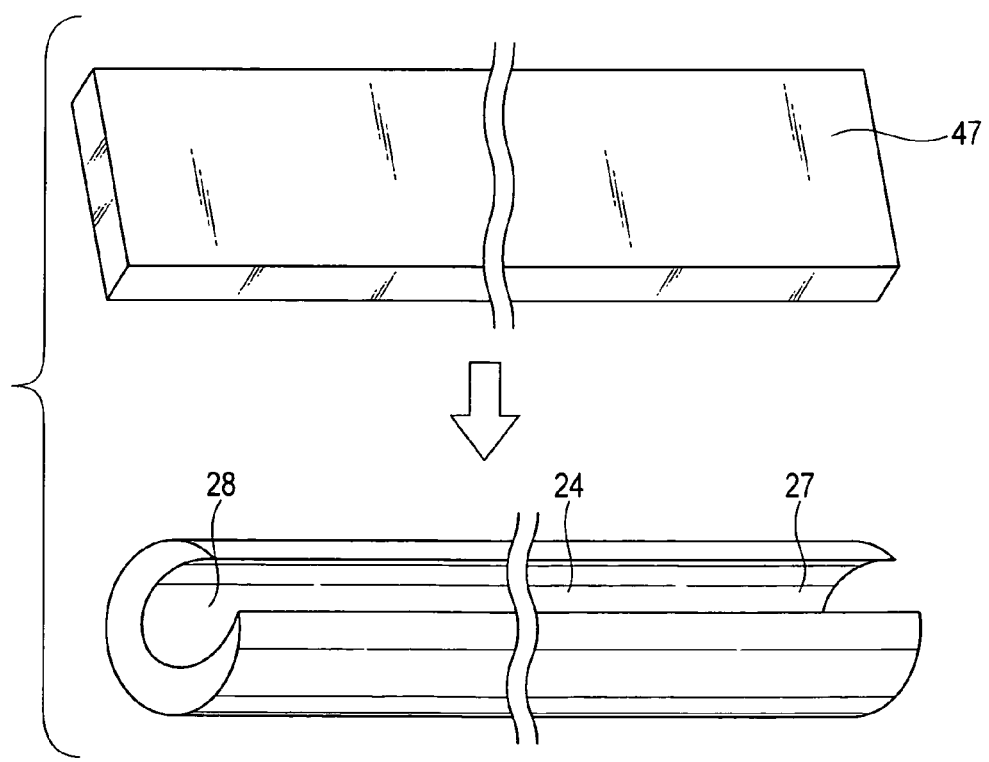
F I G. 8

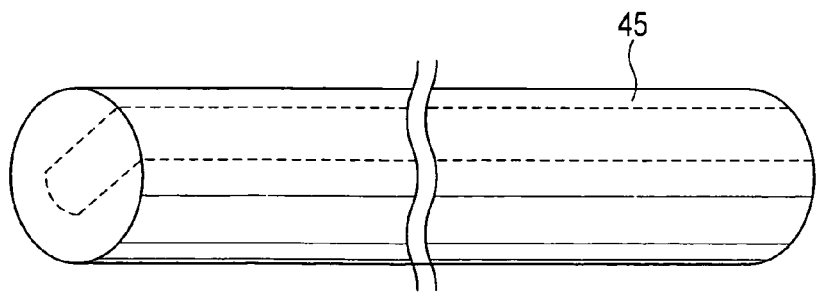
F I G. 9A
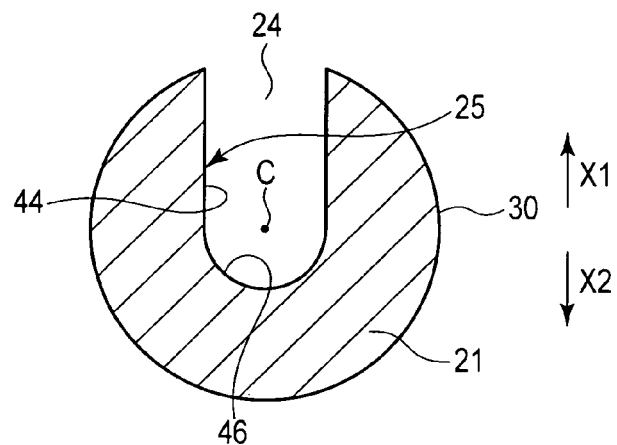
F I G. 9B
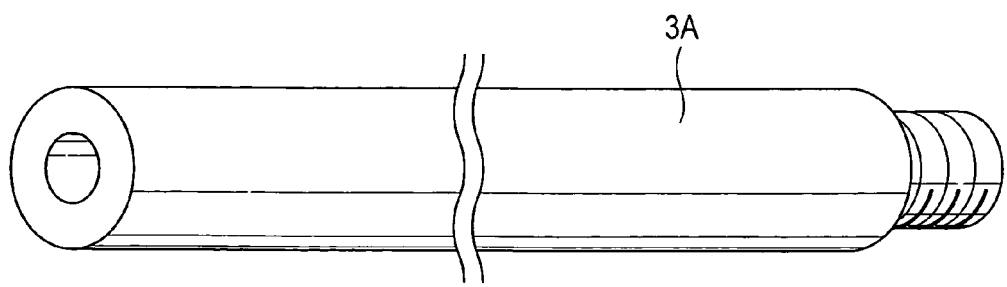
F I G. 10

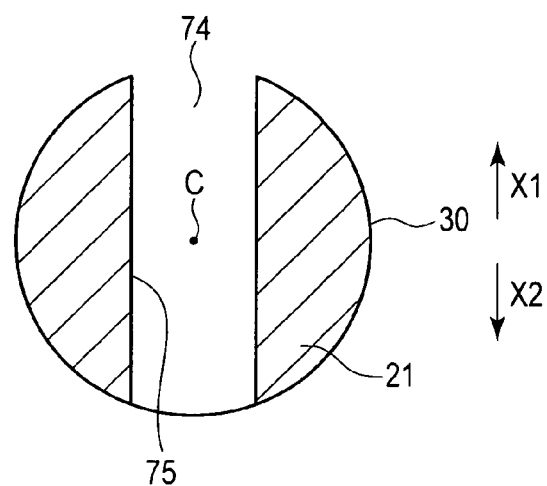
F I G. 17
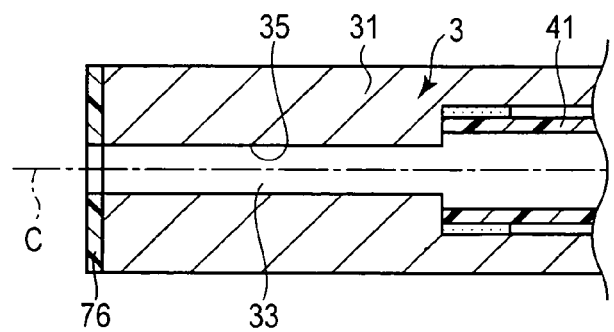
F I G. 18
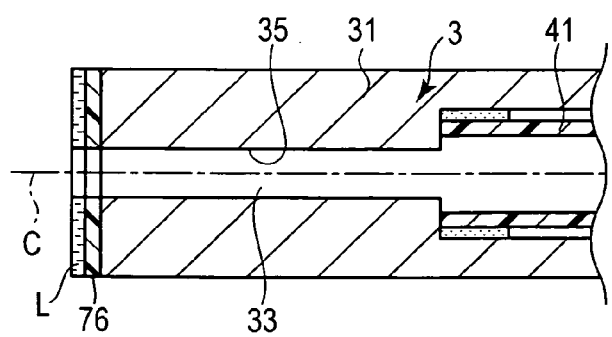
F I G. 19

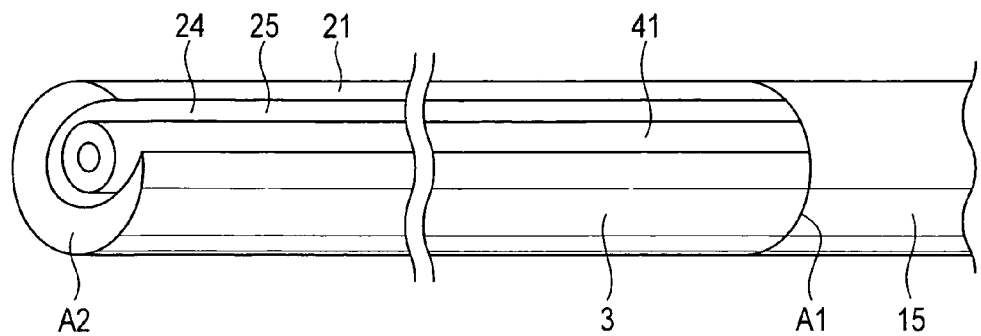
F I G. 20
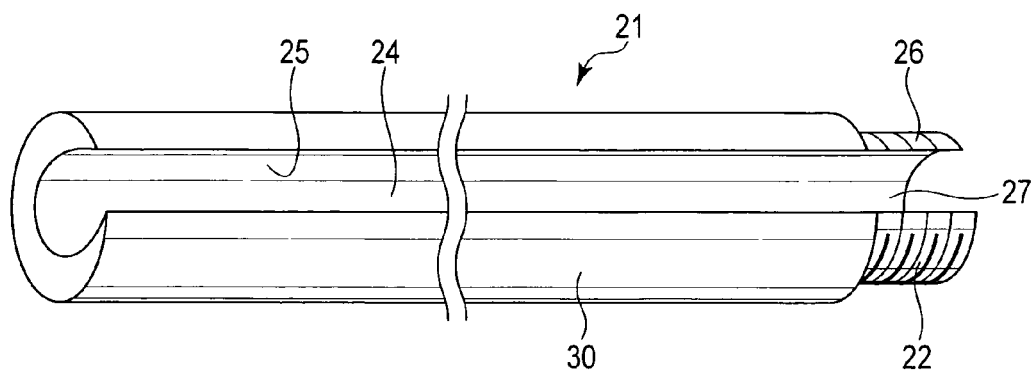
F I G. 21

ULTRASONIC PROBE

CROSS-REFERENCE TO RELATED APPLICATIONS

This is a Continuation Application of PCT Application No. PCT/JP2012/054802, filed Feb. 27, 2012 and based upon and claiming the benefit of priority from prior U.S. Provisional Application No. 61/447938, filed Mar. 1, 2011, the entire contents of which are incorporated herein by reference.

BACKGROUND OF THE INVENTION

1. Field of the Invention

The present invention relates to an ultrasonic probe used in an ultrasonic treatment device such as an ultrasonic suction device.

2. Description of the Related Art

Jpn. Pat. Appln. KOKAI Publication No. 2005-27809 has disclosed an ultrasonic treatment device configured to conduct a treatment known as ultrasonic suction and a treatment known as ultrasonic coagulation-and-cutting. This ultrasonic treatment device includes an ultrasonic probe which is configured to transmit ultrasonic vibrations from a proximal end to a distal end. The ultrasonic suction is performed by using a distal face of the ultrasonically vibrating ultrasonic probe, and is performed by using a physical phenomenon known as cavitation. More specifically, as the ultrasonic probe repeats tens of thousands of high-velocity vibrations per second by ultrasonic vibrations, pressure periodically varies in a vicinity of the distal face of the ultrasonic probe. When the pressure in the vicinity of the distal face is lower than saturated vapor pressure for only a short time because of a pressure variation, small air bubbles (cavities) are generated in a liquid within a body cavity or in a liquid supplied from the ultrasonic treatment device to a vicinity of a treatment position of the living tissue. The generated air bubbles disappear because of the force that acts when the pressure in the vicinity of the distal face increases (compression). The above-described physical phenomenon is called a cavitation phenomenon. An inelastic living tissue such as a hepatic cell is shattered and emulsified by impact energy when the air bubbles disappear. A suction path passes through an inside of the ultrasonic probe from the proximal end to the distal end. The shattered and emulsified living tissue is suctioned and collected from a suction opening at the distal end of the ultrasonic probe through the suction path. The above-described functions are continued to resect the living tissue. In this case, an elastic living tissue such as a blood vessel absorbs the impact and is therefore not easily shattered, and the living tissue is selectively shattered. However, while the living tissue is selectively shattered by the cavitation, elastic living tissue such as a blood vessel may also be damaged when the treatment by the cavitation is carried on with the distal end of the ultrasonic probe remaining at the treatment position (affected part) of the living tissue. Therefore, the treatment by the cavitation is conducted with the ultrasonic probe moving along a surface of the treatment position (affected part). As the suction path passes through the ultrasonic probe from the proximal end to the distal end, the ultrasonic probe has a cylindrical shape.

BRIEF SUMMARY OF THE INVENTION

According to one aspect of the invention, an ultrasonic probe configured to transmit ultrasonic vibrations from a proximal end to a distal end, the ultrasonic probe includes a probe body which includes an outer peripheral portion provided along a longitudinal axis; and a void defining surface which defines a void in the probe body along the longitudinal axis from a first anti-node position of the ultrasonic vibrations to a second anti-node position of the ultrasonic vibrations different from the first anti-node position, the void being open to an outside along the longitudinal axis in at least one part of the outer peripheral portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic sectional view showing the configuration of a vibrator unit according to the first embodiment;

FIG. 3 is a schematic perspective view showing an ultrasonic probe according to the first embodiment;

FIG. 5 is a sectional view showing a section of a probe body of the ultrasonic probe according to the first embodiment perpendicular to a longitudinal axis;

FIG. 6 is a schematic sectional view showing the configuration of a part between the ultrasonic probe and a horn according to the first embodiment;

FIG. 7 is a sectional view showing the configuration of a part between the probe body of the ultrasonic probe and a cylindrical portion according to the first embodiment;

FIG. 8 is a schematic diagram showing a method of manufacturing the probe body of the ultrasonic probe according to the first embodiment;

FIG. 9A is a schematic diagram showing a method of manufacturing the probe body of the ultrasonic probe according to the first embodiment different from FIG. 8;

FIG. 9B is a sectional view showing the section, which is perpendicular to the longitudinal axis, of the probe body formed by the method of manufacturing the ultrasonic probe according to the first embodiment in FIG. 9A;

FIG. 10 is a schematic perspective view showing an ultrasonic probe according to a comparative example of the first embodiment;

FIG. 17 is a sectional view showing the section, which is perpendicular to the longitudinal axis, of the probe body of the ultrasonic probe according to the fourth modification of the first embodiment;

FIG. 18 is a schematic sectional view showing the configuration of a distal portion of the ultrasonic probe according to a fifth modification of the first embodiment;

FIG. 19 is a sectional view showing an adhered state of liquid on a distal face of the ultrasonic probe according to the fifth modification of the first embodiment;

FIG. 20 is a schematic perspective view showing an ultrasonic probe according to a second embodiment of the present invention;

FIG. 21 is a schematic perspective view showing a probe body of the ultrasonic probe according to the second embodiment;

DETAILED DESCRIPTION OF THE INVENTION (First Embodiment)

Figure 1:
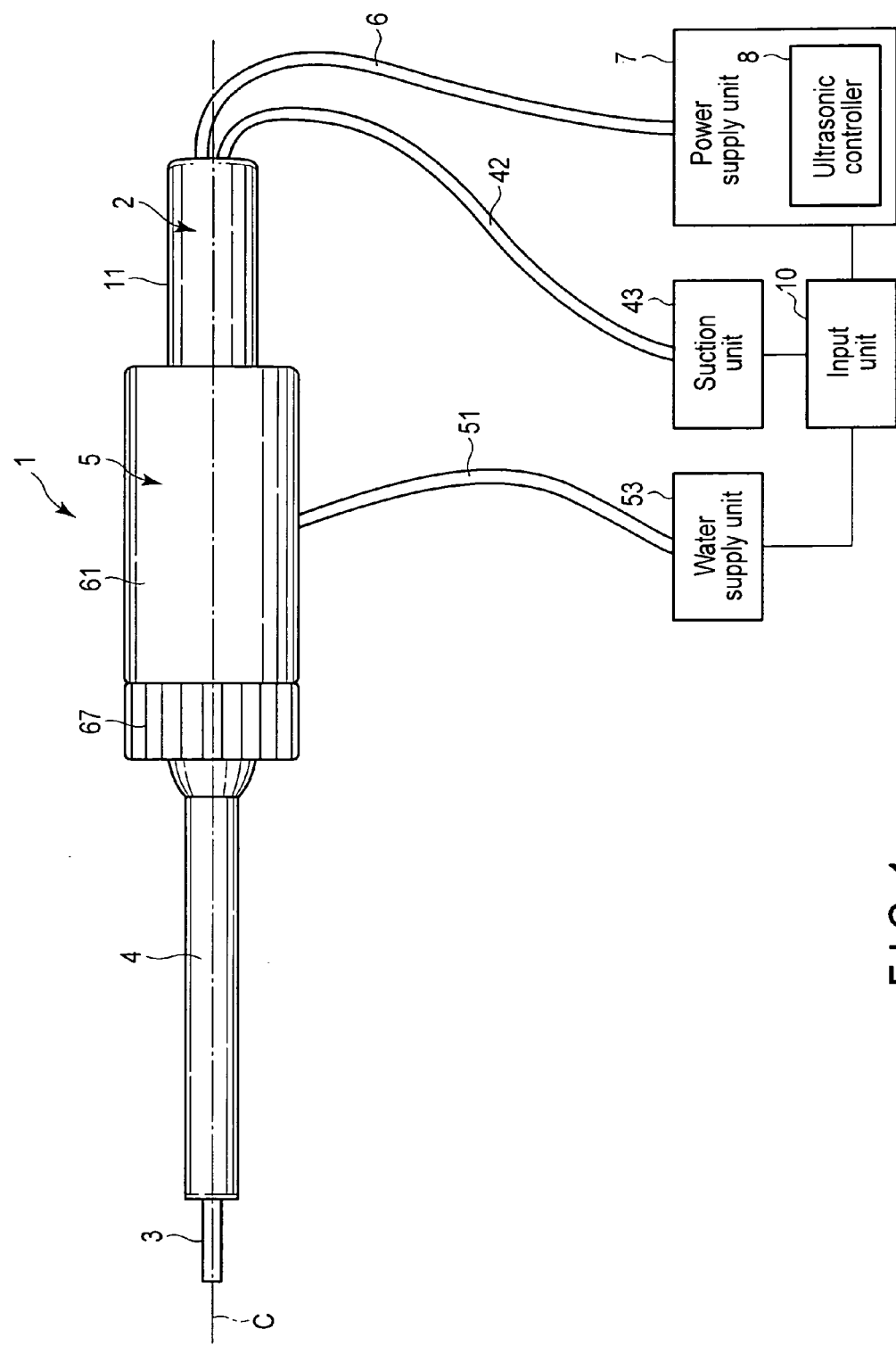
FIG. 1 is a schematic diagram showing an ultrasonic treatment device according to a first embodiment of the present invention.

A first embodiment of the present invention is described with reference to FIG. 1 to FIG. 12. FIG. 1 is a diagram showing an ultrasonic treatment device 1 according to the present embodiment. The ultrasonic treatment device 1 according to the present embodiment is an ultrasonic suction device which is configured to selectively shatter and resect living tissue by cavitation caused by ultrasonic vibrations, and configured to suction the resected living tissue.

As shown in FIG. 1, the ultrasonic treatment device 1 includes a vibrator unit 2, an ultrasonic probe (probe unit) 3, a sheath (sheath unit) 4, and a handle unit 5.

The vibrator unit 2 includes a vibrator case 11. One end of a cable 6 is connected to a proximal end of the vibrator case 11. The other end of the cable 6 is connected to a power supply unit 7. The power supply unit 7 includes an ultrasonic controller 8. An input unit 10 such as a foot switch is connected to the power supply unit 7.

FIG. 2 is a diagram showing the configuration of the vibrator unit 2. As shown in FIG. 2, an ultrasonic vibrator 12 which includes piezoelectric elements configured to convert a current to ultrasonic vibrations is provided inside the vibrator case 11.

One end of each of electric signal lines 13A and 13B is connected to the ultrasonic vibrator 12. The other end of each of the electric signal lines 13A and 13B is connected to the ultrasonic controller 8 of the power supply unit 7 through an inside of the cable 6.

Ultrasonic vibrations are generated in the ultrasonic vibrator 12 by supplying a current to the ultrasonic vibrator 12 from the ultrasonic wave controller 8 via the electric signal lines 13A and 13B. A horn 15 which is configured to increase an amplitude of the ultrasonic vibrations is coupled to a distal direction side of the ultrasonic vibrator 12. The horn 15 is attached to the vibrator case 11. In the ultrasonic vibrator 12 and the horn 15, a space portion 19 is formed about a longitudinal axis C. An internal thread 16 is formed in a distal portion of an inner peripheral surface of the horn 15.

Figure 4:
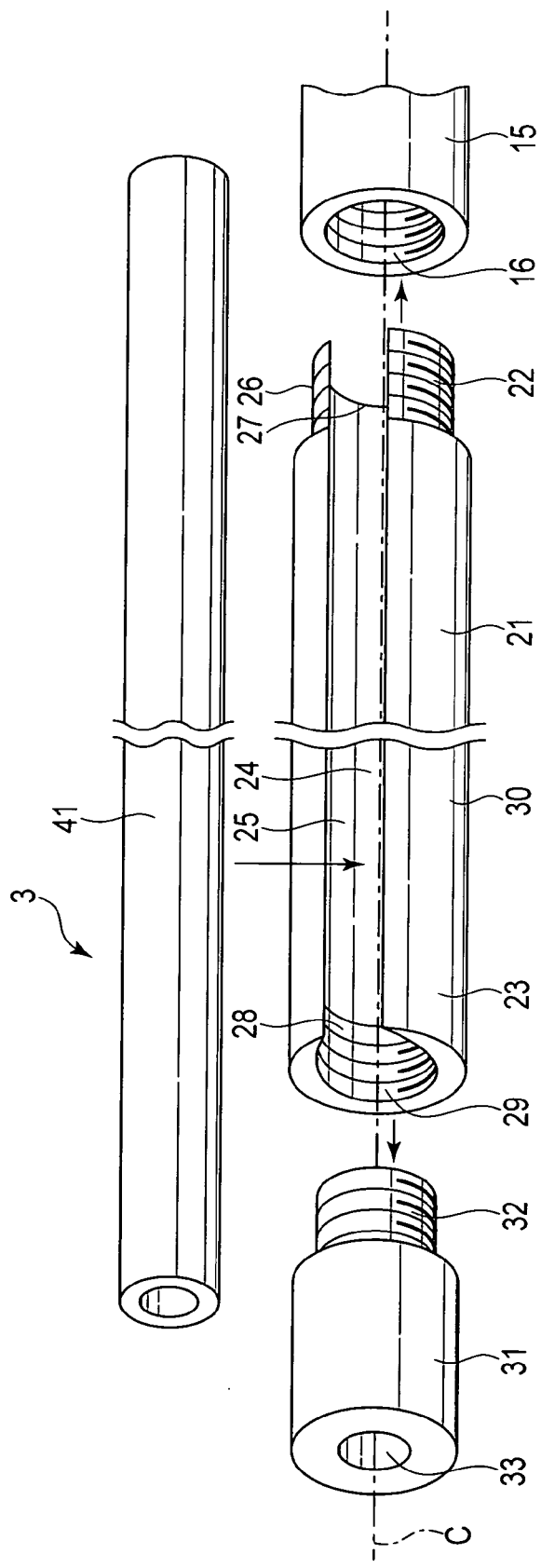
FIG. 4 is a schematic perspective view showing the ultrasonic probe according to the first embodiment disassembled into members.

FIG. 3 and FIG. 4 are diagrams showing the configuration of the ultrasonic probe 3. As shown in FIG. 3 and FIG. 4, the ultrasonic probe 3 includes a probe body 21, a cylindrical portion 31, and a tube 41.

The probe body 21 extends along the longitudinal axis C. The probe body 21 includes an outer peripheral portion 30 provided along the longitudinal axis C. A proximal connection portion 22 is provided integrally with the probe body 21 in a part to a proximal direction side of the probe body 21. A distal connection portion 23 is provided integrally with the probe body 21 in a part to the distal direction side of the probe body 21.

FIG. 5 is a diagram showing a section of the probe body 21 perpendicular to the longitudinal axis C. As shown in FIG. 4 and FIG. 5, the probe body 21 includes a groove defining surface 25 which defines a groove portion 24 along the longitudinal axis C. The groove portion 24 extends from a proximal end to a distal end of the probe body 21. The groove portion 24 is recessed from a first perpendicular direction (direction indicated by arrow X1 in FIG. 5) perpendicular to the longitudinal axis C toward a second perpendicular direction (direction indicated by arrow X2 in FIG. 5) opposite to the first perpendicular direction. The groove portion 24 is recessed toward the second perpendicular direction up to a part to a second perpendicular direction side of the longitudinal axis C.

That is, the groove portion 24 which is a void extends from the first perpendicular direction toward the second perpendicular direction. A first-perpendicular-direction-side end of the groove defining surface 25, which is a void defining surface, is continuous with the outer peripheral portion 30 of the probe body 21. The groove defining surface 25 is an arcuate curved surface in a section perpendicular to the longitudinal axis C.

As shown in FIG. 4, an external thread 26 is provided on the outer peripheral portion 30 of the proximal connection portion 22. When the external thread 26 is screwed to the internal thread 16 of the horn 15, the probe body 21 of the ultrasonic probe 3 is attached to the distal direction side of the horn 15. A proximal groove 27 communicating with a proximal end of the groove portion 24 is provided in the proximal connection portion 22. The proximal groove 27 is recessed from the first perpendicular direction toward the second perpendicular direction in the same manner as the groove portion 24.

FIG. 6 is a diagram showing the configuration of a part between the horn 15 and the ultrasonic probe 3. As shown in FIG. 3 and FIG. 6, the proximal connection portion 22 is located to an inner peripheral side of the horn 15 when the probe body 21 is attached to the horn 15. Thus, in directions parallel to the longitudinal axis C, a position of a distal end of the horn 15 substantially coincides with a position of a proximal end of the groove defining surface 25.

Therefore, when the probe body 21 is attached to the horn 15, the groove portion 24 extends along the longitudinal axis C from the distal end of the horn 15 (the proximal end of the groove defining surface 25).

As shown in FIG. 4, a distal groove 28 communicating with a distal end of the groove portion 24 is provided in the distal connection portion 23. The distal groove 28 is recessed from the first perpendicular direction toward the second perpendicular direction in the same manner as the groove portion 24. An internal thread 29 is provided on an inner peripheral portion of the distal connection portion 23.

As shown in FIG. 3 and FIG. 4, the cylindrical portion 31 is coupled to the distal direction side of the probe body 21. An external thread 32 is provided on a proximal portion of an outer peripheral portion of the cylindrical portion 31. When the external thread 32 is screwed to the internal thread 29 of the distal connection portion 23, the cylindrical portion 31 is coupled to the probe body 21.

FIG. 7 is a diagram showing the configuration of a part between the probe body 21 and the cylindrical portion 31. As shown in FIG. 3 and FIG. 7, the distal connection portion 23 is located to an outer peripheral side of the cylindrical portion 31 when the cylindrical portion 31 is coupled to the probe body 21. Thus, in the directions parallel to the longitudinal axis C, a position of a proximal end of the cylindrical portion 31 substantially coincides with a position of a distal end of the groove defining surface 25. Therefore, when the cylindrical portion 31 is coupled to the probe body 21, the groove portion 24 extends along the longitudinal axis C up to the proximal end of the cylindrical portion 31 (the distal end of the groove defining surface 25). When the cylindrical portion 31 is coupled to the probe body 21, an inside of the cylindrical portion 31 is in communication with the groove portion 24.

As described above, when the probe body 21 is attached to the horn 15 and the cylindrical portion 31 is coupled to the probe body 21, the ultrasonic vibrations generated in the ultrasonic vibrator 12 are transmitted to s distal end of the cylindrical portion 31 via the horn 15 and the probe body 21. That is, the ultrasonic vibrations are transmitted from the proximal end to the distal end of the ultrasonic probe 3. In this case, a vibration transmitting portion 20 configured to transmit the ultrasonic vibrations is formed by the horn 15, the probe body 21, and the cylindrical portion 31. The ultrasonic vibrations are longitudinal vibrations having a vibration transmission direction and a vibration direction coinciding with each other.

When the probe body 21 is attached to the horn 15 and the cylindrical portion 31 is coupled to the probe body 21, the distal end of the horn 15 (the proximal end of the groove defining surface 25) is at a first anti-node position A1 of the ultrasonic vibrations. The proximal end of the cylindrical portion 31 (the distal end of the groove defining surface 25) is at a second anti-node position A2 of the ultrasonic vibrations different from the first anti-node position A1. When the probe body 21 is attached to the horn 15 and the cylindrical portion 31 is coupled to the probe body 21, the groove portion 24 extends from the distal end of the horn 15 to the proximal end of the cylindrical portion 31. Therefore, when the probe body 21 is attached to the horn 15 and the cylindrical portion 31 is coupled to the probe body 21, the groove portion 24 is defined by the groove defining surface 25 from the first anti-node position A1 to the second anti-node position A2 along the longitudinal axis C.

Here, at the first anti-node position A1, a sectional shape of the vibration transmitting portion 20 perpendicular to the transmission direction and vibration direction (longitudinal axis C) of the ultrasonic vibrations changes. That is, the sectional shape of the vibration transmitting portion 20 perpendicular to the longitudinal axis C changes at the first anti-node position A1 from a cylindrical shape, 5. which is point-symmetrical about the longitudinal axis C, to a recessed shape, which is not point-symmetrical about the longitudinal axis C. Similarly, at the second anti-node position A2, the sectional shape of the vibration transmitting portion 20 perpendicular to the transmission direction and vibration direction (longitudinal axis C) of the ultrasonic vibrations changes. That is, the sectional shape of the vibration transmitting portion 20 perpendicular to the longitudinal axis C changes at the second anti-node position A2 from the recessed shape, which is not point-symmetrical about the longitudinal axis C, to the cylindrical shape, which is point-symmetrical about the longitudinal axis C.

When the probe body 21 is attached to the horn 15 and the cylindrical portion 31 is coupled to the probe body 21, the distal end of the cylindrical portion 31 is at a third anti-node position A3 of the ultrasonic vibrations different from the first anti-node position A1 and the second anti-node position A2. Cavitation is caused by a transmission of the ultrasonic vibrations to the distal end of the cylindrical portion 31 (ultrasonic probe 3). Living tissue having low elasticity such as a hepatic cell is selectively shattered and emulsified by the cavitation. In this case, living tissue having high elasticity such as a blood vessel is not shattered by the cavitation.

Steps are preferably provided in the outer peripheral portions of the probe body 21 and the cylindrical portion 31. This allows the amplitude of the ultrasonic vibrations to be increased.

As shown in FIG. 3 and FIG. 4, the tube 41 extends through the groove portion 24 along the longitudinal axis C. The tube 41 is made of a heat-resistant resin. As shown in FIG. 7, the cylindrical portion 31 includes a path defining surface 35 which defines a suction path 33 communicating with the inside of the tube 41. A distal end of the tube 41 is connected to a proximal end of the path defining surface 35. The distal end of the tube 41 is fixed to the cylindrical portion 31, for example, by an adhesive material 34, and is connected to the path defining surface 35. The distal end of the tube 41 may be connected to the path defining surface 35 by means other than the adhesive material 34. For example, an elastic member may be attached to an outer peripheral portion of the tube 41 by a heat-resistant rubber lining, and the distal end of the tube 41 may be fixed to the cylindrical portion 31 by the elastic member and connected to the path defining surface 35. An internal thread provided on an inner peripheral portion of the cylindrical portion 31 may be screwed to an external thread provided on the outer peripheral portion of the tube 41 to fix the distal end of the tube 41 to the cylindrical portion 31 and connect the distal end of the tube 41 to the path defining surface 35.

When the probe body 21 is attached to the horn 15 and the cylindrical portion 31 is coupled to the probe body 21, a first node position (node position) B1 of the ultrasonic vibrations is located at an intermediate position between the proximal end of the cylindrical portion 31 and the distal end of the cylindrical portion 31. In this case, the path defining surface 35 is provided from the first node position B1 up to the third anti-node position A3 along the longitudinal axis C. That is, a proximal end of the path defining surface 35 is at the first node position B1, and a distal end of the path defining surface 35 is at the third anti-node position A3. As described above, the distal end of the tube 41 is connected to the proximal end of the path defining surface 35. Therefore, the distal end of the tube 41 is connected to the path defining surface 35 at the first node position B1.

The cylindrical portion 31 includes a hole defining surface 37 defining an insertion hole 36 through which the tube 41 is inserted. A diameter of the insertion hole 36 is formed to be much greater than an outside diameter of the tube 41. When the probe body 21 is attached to the horn 15 and the cylindrical portion 31 is coupled to the probe body 21, the hole defining surface 37 is provided from the second anti-node position A2 up to the first node position B1 along the longitudinal axis C. That is, a proximal end of the hole defining surface 37 is at the second anti-node position A2, and a distal end of the hole defining surface 37 is at the first node position B1. The path defining surface 35 is continuous to the distal direction side of the hole defining surface 37.

A sectional area of the suction path 33 perpendicular to the longitudinal axis C is defined to be less than a sectional area of the insertion hole 36 perpendicular to the longitudinal axis C. The sectional area of the suction path 33 perpendicular to the longitudinal axis C is preferably less than an area of a part surrounded by an inner peripheral portion of the tube 41 in a section perpendicular to the longitudinal axis C.

As shown in FIG. 6, a proximal end of the tube 41 is connected to the horn 15 at a position to the proximal direction side of the distal end of the horn 15. When the probe body 21 is attached to the horn 15 and the cylindrical portion 31 is coupled to the probe body 21, the position at which the proximal end of the tube 41 is connected to the horn 15 is a second node position B2. The distal end of the horn 15 is at the first anti-node position A1 of the ultrasonic vibrations. Therefore, the second node position B2 is located to the proximal direction side of the first anti-node position A1. The proximal end of the tube 41 is connected to the horn 15 in the same manner as the connection of the distal end of the tube 41 to the path defining surface 35.

When the proximal end of the tube 41 is connected to the horn 15, the inside of the tube 41 communicates with the space portion 19 provided inside the ultrasonic vibrator 12 and the horn 15. As shown in FIG. 2, one end of a suction tube 42 is connected to the space portion 19. As shown in FIG. 1, the suction tube 42 extends to an outside of the vibrator case 11, and the other end of the suction tube 42 is connected to a suction unit 43. The suction unit 43 is connected to the input unit 10. When the living tissue resected by the cavitation is suctioned, the suction unit 43 is driven, for example, by an input in the input unit 10. If the suction unit 43 is driven, the resected living tissue is suctioned into the suction path 33. The living tissue is then suctioned to the suction unit 43 through the inside of the tube 41, the space portion 19, and an inside of the suction tube 42 in order.

The tube 41 has its distal end fixed to the cylindrical portion 31, and its proximal end fixed to the horn 15. Thus, the tube 41 may be fixed to the probe body 21, or does not have to be fixed to the probe body 21. When the tube 41 is fixed to the probe body 21, the tube 41 is fixed to the probe body 21 at a node position different from the first node position B1 and the second node position B2. The tube 41 is fixed to the probe body 21, for example, by an adhesive material. An elastic member may be attached to the outer peripheral portion of the tube 41 by a heat-resistant rubber lining, and the tube 41 may be fixed to the probe body 21 by the elastic member. Alternatively, an elastic member may be attached to the groove defining surface 25 by a heat-resistant rubber lining, and the tube 41 may be fixed to the probe body 21 by the elastic member.

Here, a method of manufacturing the ultrasonic probe 3 is described. In order to manufacture the ultrasonic probe 3, the probe body 21 is first formed. FIG. 8 is a diagram showing a method of manufacturing the probe body 21. As shown in FIG. 8, a flat plate member 47 is bent in order to form the probe body 21, the proximal connection portion 22, and the distal connection portion 23. Thus, the groove portion 24, the proximal groove 27, and the distal groove 28 are formed. The shape of the probe body 21 including the proximal connection portion 22 and the distal connection portion 23 is formed, for example, by cutting.

FIG. 9A is a diagram showing another method of manufacturing the probe body 21, the proximal connection portion 22, and the distal connection portion 23. As shown in FIG. 9A, in order to form the probe body 21, a columnar member 45 is milled (fraise) (milled) to cut a part indicated by a dotted line in FIG. 9A. In this way, the groove portion 24, the proximal groove 27, and the distal groove 28 are formed. The probe body 21, the proximal connection portion 22, and the distal connection portion 23 may be formed by forging.

Here, when the probe body 21 is manufactured by the method shown in FIG. 8, the groove defining surface 25 is preferably an arcuate curved surface in the section perpendicular to the longitudinal axis C. When the probe body 21 is manufactured by the method shown in FIG. 9A, the groove defining surface 25 preferably includes a plane 44, and a curved surface 46 provided to the second perpendicular direction side of the plane 44, as shown in FIG. 9B. In this case, the plane 44 extends parallel to the longitudinal axis C and from the first perpendicular direction toward the second perpendicular direction. The curved surface 46 is arcuate in the section perpendicular to the longitudinal axis C. Milling can be easily performed by forming the groove defining surface 25 in this way. Thus, the probe body 21 is more easily manufactured at low cost.

After the probe body 21 including the proximal connection portion 22 and the distal connection portion 23 has been formed as described above, the cylindrical portion 31 is coupled to the distal direction side of the probe body 21. The tube 41 is then disposed in the groove portion 24 along the longitudinal axis C. The distal end of the tube 41 is then connected to the cylindrical portion 31. As described above, the groove portion 24 is recessed toward the second perpendicular direction up to the part to the second perpendicular direction side of the longitudinal axis C. That is, the groove portion 24, which is a void, extends toward the second perpendicular direction up to the part to the second perpendicular direction side of the longitudinal axis C. This allows the distal end of the tube 41 disposed in the groove portion 24 to be easily connected to the cylindrical portion 31. In this way, the ultrasonic probe 3 is formed.

Here, as a comparative example, suppose an ultrasonic probe 3A that is cylindrically shaped over an entire dimension along the longitudinal axis C, as shown in FIG. 10. The ultrasonic probe 3A is formed by the perforation of a columnar member (not shown). Here, the columnar member to be the material of the ultrasonic probe 3A has a long dimension along the longitudinal axis C and a small dimension in direction perpendiculars perpendicular to the longitudinal axis C. The perforation of this elongated columnar member by using a special drill requires a long time, and leads to an increased cost.

On the other hand, in the ultrasonic probe 3 according to the present embodiment, the probe body 21, having the groove portion 24 formed therein, accounts for a large part of a dimension of the ultrasonic probe 3 along the longitudinal axis C. As described above, the probe body 21 is formed in a shorter time and at a lower cost than the perforation of the columnar member. The cylindrical portion 31 that needs to be perforated has a small dimension along the longitudinal axis C. Thus, the time required for the perforation is shorter than the time required for the formation of the ultrasonic probe 3A. Consequently, the ultrasonic probe 3 is efficiently manufactured at low cost.

Figure 11:
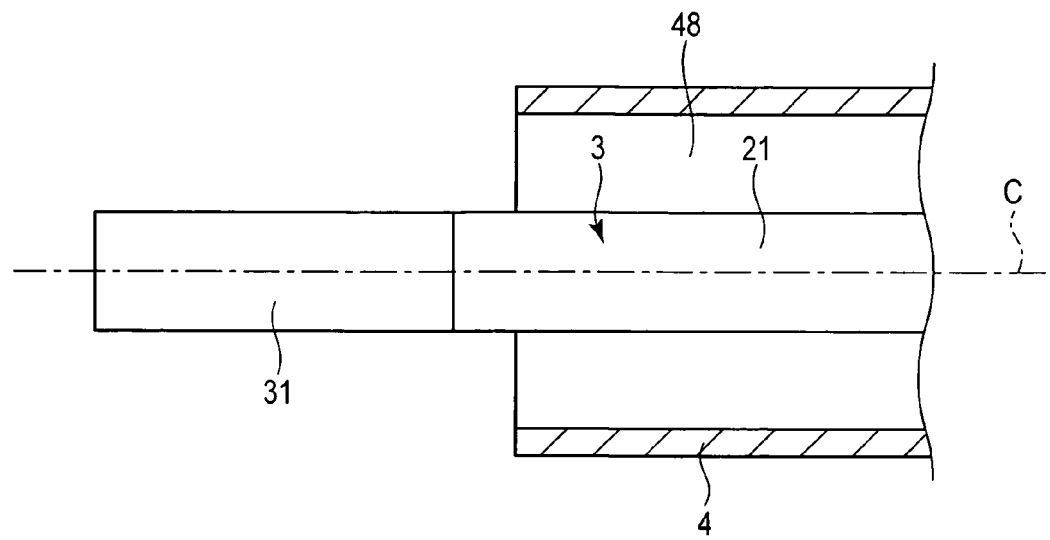
FIG. 11 is a schematic sectional view showing a state in which the ultrasonic probe is inserted through a sheath according to the first embodiment.

As shown in FIG. 1, the ultrasonic probe 3 is inserted through the sheath 4. FIG. 11 is a diagram showing a state in which the ultrasonic probe 3 is inserted through the sheath 4. As shown in FIG. 11, when the ultrasonic probe 3 is inserted through the sheath 4, a water supply path 48 is formed between the outer peripheral portion of the ultrasonic probe 3 and the inner peripheral portion of the sheath 4. That is, the water supply path 48 is defined by the outer peripheral portion of the ultrasonic probe 3 and the inner peripheral portion of the sheath 4.

Figure 12:
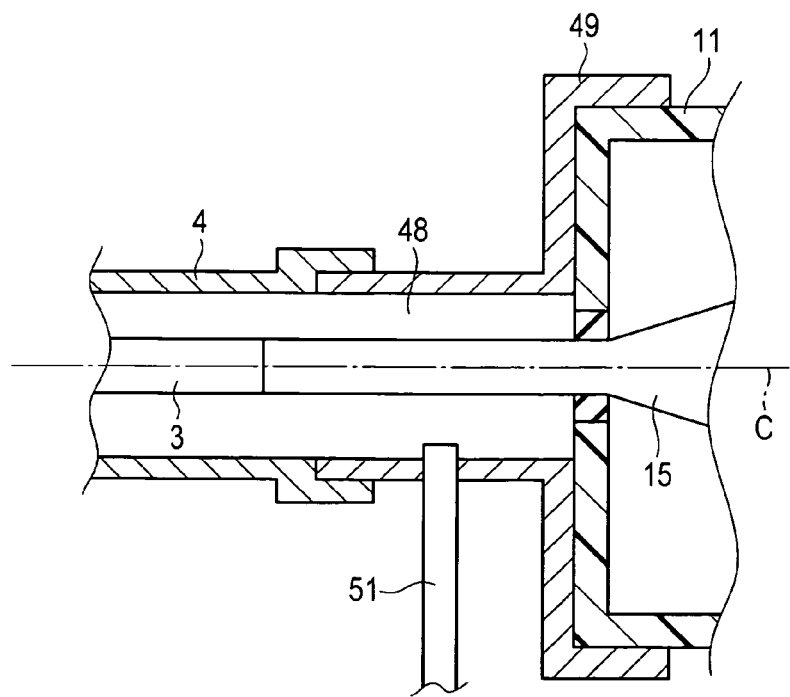
FIG. 12 is a schematic sectional view showing the configuration of a coupling portion between the sheath and a vibrator case according to the first embodiment.

FIG. 12 is a schematic diagram showing the configuration of a coupling portion between the sheath 4 and the vibrator case 11. A distal portion of a cylindrical intermediary member 49 is attached to a proximal portion of the sheath 4. The sheath 4 is rotatable relative to the intermediary member 49 around the longitudinal axis C. A distal portion of the vibrator case 11 is attached to a proximal portion of the intermediary member 49.

The water supply path 48 formed between the ultrasonic probe 3 and the sheath 4 extends up to a distal face of the vibrator case 11. One end of a water supply tube 51 is connected to an inside of the intermediary member 49. As shown in FIG. 1, the water supply tube 51 extends to an outside of the handle unit 5, and the other end of the water supply tube 51 is connected to a water supply unit 53. The water supply unit 53 is connected to the input unit 10. If the water supply unit 53 is driven, for example, by an input in the input unit 10, water (liquid) passes through an inside of the water supply tube 51 and the water supply path 48 in order. The water is then supplied to, for example, the living tissue from a clearance located between the distal end of the sheath 4 and the ultrasonic probe 3. For example, a bleeding part is checked and a body cavity is washed by the water supply. In ultrasonic suction, a liquid such as a physiological saline is supplied to a vicinity of a treatment position from the water supply unit 53.

As shown in FIG. 1, the handle unit 5 includes a cylindrical case 61. The cylindrical case 61 is attached to the vibrator case 11. A rotational operation knob 67 is coupled to the distal direction side of the cylindrical case 61. The rotational operation knob 67 is rotatable relative to the cylindrical case 61 around the longitudinal axis C. The sheath 4 is attached to the inner peripheral side of the rotational operation knob 67. If the rotational operation knob 67 is rotated, the ultrasonic probe 3 and the sheath 4 rotate around the longitudinal axis C together with the rotational operation knob 67.

Now, the functions of the ultrasonic treatment device 1 according to the present embodiment are described. To ultrasonically suction living tissue by using the ultrasonic treatment device 1, ultrasonic vibrations are generated in the ultrasonic vibrator 12 by supplying the current to the ultrasonic vibrator 12 from the ultrasonic controller 8 via the electric signal lines 13A and 13B. The ultrasonic vibrations are transmitted from the proximal end to the distal end of the vibration transmitting portion 20 (ultrasonic probe 3).

Here, at the first anti-node position A1 located at the proximal end of the groove defining surface 25 (the distal end of the horn 15), the sectional shape of the vibration transmitting portion 20 perpendicular to the transmission direction and vibration direction (longitudinal axis C) of the ultrasonic vibrations changes. That is, the sectional shape of the vibration transmitting portion 20 perpendicular to the longitudinal axis C changes at the first anti-node position A1 from the cylindrical shape, which is point-symmetrical about the longitudinal axis C, to the recessed shape, which is not point-symmetrical about the longitudinal axis C. At the position where the sectional shape of the vibration transmitting portion 20 perpendicular to the transmission direction and vibration direction of the ultrasonic vibrations greatly changes, the ultrasonic vibrations are easily influenced by stress in directions perpendicular to the longitudinal axis C. Because of the influence of the stress, a vibration mode of the ultrasonic vibrations changes, and the ultrasonic vibrations are not properly transmitted to the distal end of the ultrasonic probe 3.

Therefore, according to the present embodiment, the sectional shape of the vibration transmitting portion 20 perpendicular to the transmission direction and vibration direction of the ultrasonic vibrations is set to greatly change at the first anti-node position A1. At the anti-node position of the ultrasonic vibrations including the first anti-node position A1, displacement caused by the vibrations is maximized, but the stress in the directions perpendicular to the longitudinal axis C is zero. Therefore, the stress does not act on the ultrasonic vibrations at the first anti-node position A1 where the sectional shape of the vibration transmitting portion 20 perpendicular to the transmission direction and the vibration direction of the ultrasonic vibrations greatly changes. Accordingly, the vibration mode does not change.

Similarly, in the ultrasonic probe 3, the sectional shape of the vibration transmitting portion 20 perpendicular to the transmission direction and vibration direction of the ultrasonic vibrations is set to greatly change at the second anti-node position A2 located at the distal end of the groove defining surface 25 (the proximal end of the cylindrical portion 15). As described above, at the second anti-node position A2, displacement caused by the vibrations is maximized, but the stress in the directions perpendicular to the longitudinal axis C is zero. Therefore, the stress does not act on the ultrasonic vibrations at the second anti-node position A2 where the sectional shape of the vibration transmitting portion 20 perpendicular to the transmission direction and the vibration direction of the ultrasonic vibrations greatly changes. Accordingly, the vibration mode does not change.

When the position, where the sectional shape of the vibration transmitting portion 20 perpendicular to the transmission direction and the vibration direction of the ultrasonic vibrations greatly changes, is provided as described above, the ultrasonic vibrations are set to be free of the influence of the stress in the directions perpendicular to the longitudinal axis C. Therefore, the ultrasonic vibrations are properly transmitted to the distal end of the ultrasonic probe 3.

In ultrasonic suction, a liquid such as a physiological saline is supplied to the vicinity of the treatment position from the water supply unit 53. Cavitation is caused by the transmission of the ultrasonic vibrations to the distal end of the cylindrical portion 31 (ultrasonic probe 3) accompanied by the water supply. Living tissue having low elasticity such as a hepatic cell is selectively shattered and resected by the cavitation. Here, the cylindrical portion 31 is coupled to the distal direction side of the probe body 21, and the distal face of the ultrasonic probe 3 is thereby formed into a cylindrical shape. For example, when the distal end of the probe body 21 forms the distal end of the ultrasonic probe, the distal face of the ultrasonic probe 3 is formed into a recessed shape. When the distal face is formed into a cylindrical shape, the surface area of the distal face of the ultrasonic probe 3 is greater than when the distal face is formed into a recessed shape. As the surface area of the distal face of the ultrasonic probe 3 is greater, cavitation is efficiently caused, and the living tissue is efficiently and safely shattered and resected. As the distal end of the cylindrical portion 31 (ultrasonic probe 3) is at the third anti-node position A3 of the ultrasonic vibrations, cavitation is efficiently caused by the transmission of the ultrasonic vibrations to the distal end of the cylindrical portion 31.

The distal end of the tube 41 is connected to the path defining surface 35 of the cylindrical portion 31 at the first node position B1. The proximal end of the tube 41 is connected to the horn 15 at the second node position B2. At the node position of the ultrasonic vibrations including the first node position B1 and the second node position B2, the stress in the directions perpendicular to the longitudinal axis C is maximized, but displacement caused by the vibrations is zero. Therefore, the tube 41 is firmly fixed to the cylindrical portion 31 and the horn 15 even if the vibration transmitting portion 20 (ultrasonic probe 3) ultrasonically vibrates.

When the living tissue is resected by the cavitation, the resected living tissue is suctioned. The suction unit 43 is driven, and the resected living tissue is thereby suctioned into the suction path 33. The living tissue is then suctioned to the suction unit 43 through the inside of the tube 41, the space portion 19, and the inside of the suction tube 42 in order.

Here, the sectional area of the suction path 33 perpendicular to the longitudinal axis C is less than the area of a part surrounded by the inner peripheral portion of the tube 41 in the section perpendicular to the longitudinal axis C. This prevents the living tissue suctioned from the suction path 33 from remaining in the tube 41. As a result, the living tissue resected by the cavitation is more stably suctioned.

Accordingly, the ultrasonic probe 3 having the configuration described above provides the following advantageous effects. That is, in the ultrasonic probe 3, the probe body 21 in which the groove portion 24 formed accounts for the large part of the dimension of the ultrasonic probe 3 along the longitudinal axis C. The probe body 21 provided with the groove portion 24 is formed in a shorter time and at a lower cost than the perforation of the columnar member. The cylindrical portion 31 that needs to be perforated has the small dimension along the longitudinal axis C in the ultrasonic probe 3. Thus, the time required for the perforation is shorter. Consequently, the ultrasonic probe 3 can be efficiently manufactured at low cost.

In the ultrasonic probe 3, the sectional shape of the vibration transmitting portion 20 perpendicular to the transmission direction and the vibration direction of the ultrasonic vibrations is set to greatly change at the first anti-node position A1. Similarly, in the ultrasonic probe 3, the sectional shape of the vibration transmitting portion 20 perpendicular to the transmission direction and the vibration direction of the ultrasonic vibrations is set to greatly change at the second anti-node position A2 located at the distal end of the groove defining surface 25 (the proximal end of the cylindrical portion 31). At the anti-node position of the ultrasonic vibrations including the first anti-node position A1 and the second anti-node position A2, displacement caused by the vibrations is maximized, but the stress in the directions perpendicular to the longitudinal axis C is zero. Therefore, the stress does not act on the ultrasonic vibrations at the first anti-node position A1 and the second anti-node position A2, where the sectional shape of the vibration transmitting portion 20 perpendicular to the transmission direction and the vibration direction of the ultrasonic vibrations greatly changes. Accordingly, the vibration mode does not change. As described above, even when the position where the sectional shape of the vibration transmitting portion 20 perpendicular to the transmission direction and the vibration direction of the ultrasonic vibrations greatly changes is provided, the ultrasonic vibrations are set to be free of the influence of the stress in the directions perpendicular to the longitudinal axis C. Therefore, the ultrasonic vibrations can be properly transmitted to the distal end of the ultrasonic probe 3.

In the ultrasonic probe 3, the cylindrical portion 31 is coupled to the distal direction side of the probe body 21, so that the distal face of the ultrasonic probe 3 is formed into a cylindrical shape. When the distal face is formed into a cylindrical shape, the surface area of the distal face of the ultrasonic probe 3 is greater than when the distal face is formed into a recessed shape. As the surface area of the distal face of the ultrasonic probe 3 is greater, cavitation is efficiently caused, and the living tissue can be efficiently and safely shattered and resected. As the distal end of the cylindrical portion 31 (ultrasonic probe 3) is at the third anti-node position A3 of the ultrasonic vibrations, cavitation can be more efficiently caused by the transmission of the ultrasonic vibrations to the distal end of the cylindrical portion 31.

In the ultrasonic probe 3, the distal end of the tube 41 is connected to the path defining surface 35 of the cylindrical portion 31 at the first node position B1. The proximal end of the tube 41 is connected to the horn 15 at the second node position B2. At the node position of the ultrasonic vibrations including the first node position B1 and the second node position B2, the stress in the directions perpendicular to the longitudinal axis C is maximized, but displacement caused by the vibrations is zero. Therefore, the tube 41 can be firmly fixed to the cylindrical portion 31 and the horn 15 even if the vibration transmitting portion 20 (ultrasonic probe 3) ultrasonically vibrates.

In the ultrasonic probe 3, the groove portion 24 extends toward the second perpendicular direction up to the part to the second perpendicular direction side of the longitudinal axis C. This allows the distal end of the tube 41 disposed in the groove portion 24 to be easily connected to the cylindrical portion 31.

(Modifications of First Embodiment)

Figure 13:
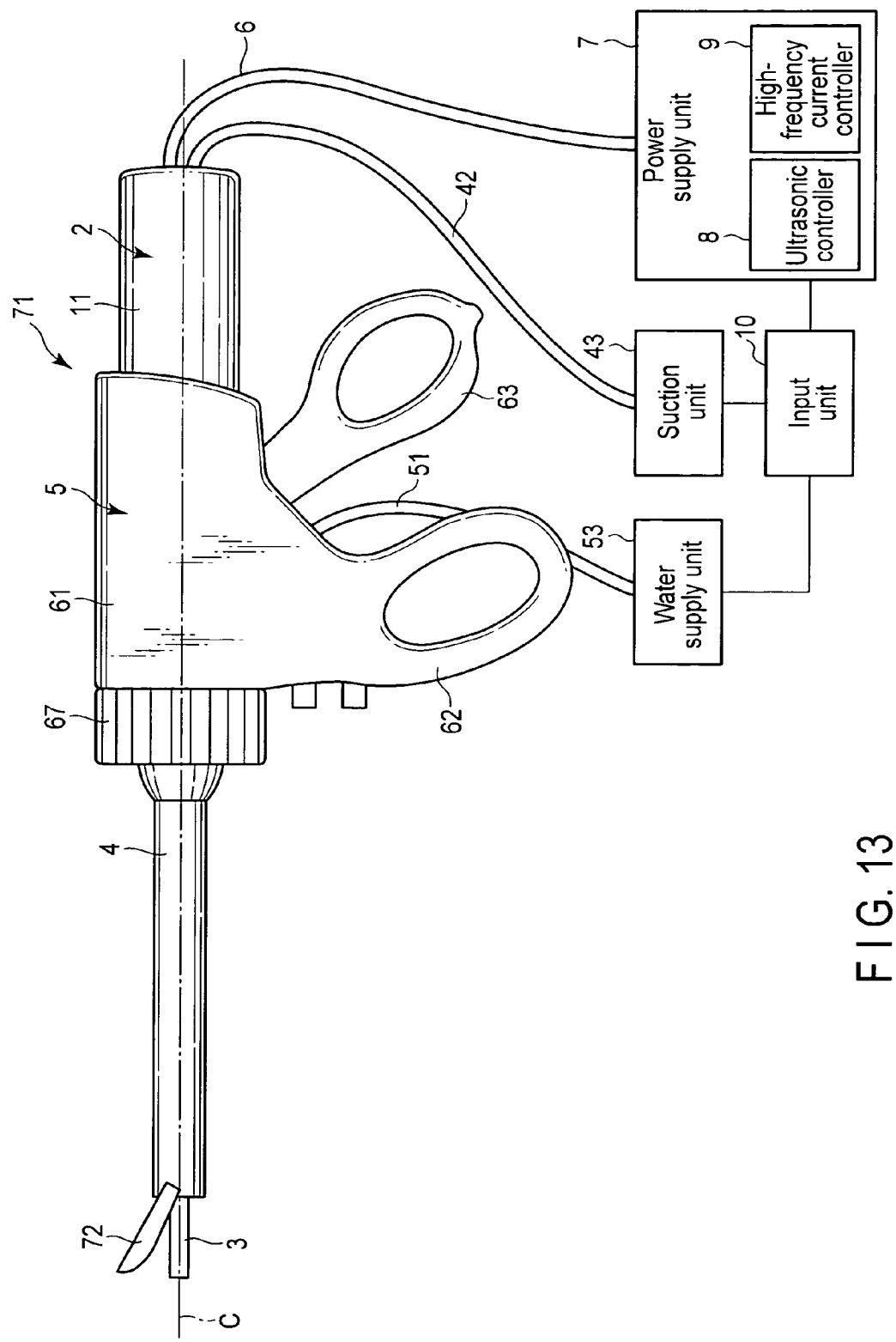
FIG. 13 is a schematic diagram showing the ultrasonic treatment device according to a first modification of the first embodiment.

According to the first embodiment, the ultrasonic treatment device 1 only performs ultrasonic suction to selectively shatter and resect the living tissue by the cavitation caused by the water supply and the ultrasonic vibrations and to suction the resected living tissue. However, the present invention is not limited thereto. For example, as a first modification, an ultrasonic treatment device 71 may coagulate and cut living tissue such as a blood vessel grasped between the ultrasonic probe 3 and a jaw 72, as shown in FIG. 13. In the ultrasonic treatment device 71, the handle unit 5 includes a fixed handle 62, and a movable handle 63 configured to open/close relative to the fixed handle 62. The jaw 72 is attached to a distal portion of the sheath 4. The movable handle 63 is opened/closed relative to the fixed handle 62, and a movable member (not shown) provided in the sheath 4 thereby moves along the longitudinal axis C. Thus, the jaw 72 opens/closes relative to the distal portion of the ultrasonic probe 3.

In the ultrasonic treatment device 71, the power supply unit 7 includes a high-frequency current controller 9. In addition to the electric signal lines 13A and 13B, an electric signal line (not shown) extending from the high-frequency current controller 9 of the power supply unit 7 through the inside of the cable 6 is connected to the ultrasonic vibrator 12. Thus, a probe side current path of the high-frequency current is formed from the high-frequency current controller 9 to the distal portion of the ultrasonic probe 3 through the ultrasonic vibrator 12 and the horn 15. An electric signal line (not shown) extending from the high-frequency current controller 9 of the power supply unit 7 through the cable 6 is connected to the vibrator case 11. The vibrator case 11 and the intermediary member 49 include electric conducting portions (not shown) configured to electrically connect the electric signal line from the high-frequency current controller 9 to the sheath 4. Accordingly, a jaw side current path of the high-frequency current is formed from the high-frequency current controller 9 to the jaw 72 through the electric conducting portion of the vibrator case 11 and the sheath 4. The ultrasonic vibrator 12 and the horn 15 are insulated from the vibrator case 11. Similarly, the sheath 4 is insulated from the ultrasonic probe 3.

Living tissue having high elasticity such as a blood vessel, which is not shattered by the cavitation, is treated between the jaw 72 and the distal portion of the ultrasonic probe 3. Frictional heat is generated between the ultrasonic probe 3 and the living tissue by the ultrasonic vibrations of the ultrasonic probe 3. The living tissue is cut by the generated frictional heat. The living tissue is also reformed by the passage of a high-frequency current between the jaw 72 and the distal portion of the ultrasonic probe 3 through the living tissue. As a result, the living tissue is coagulated.

As described above, the ultrasonic treatment device (1, 71) may include a treatment function in addition to the ultrasonic suction to selectively shatter and resect the living tissue by the cavitation caused by the ultrasonic vibrations and to suction the resected living tissue.

Figure 14:
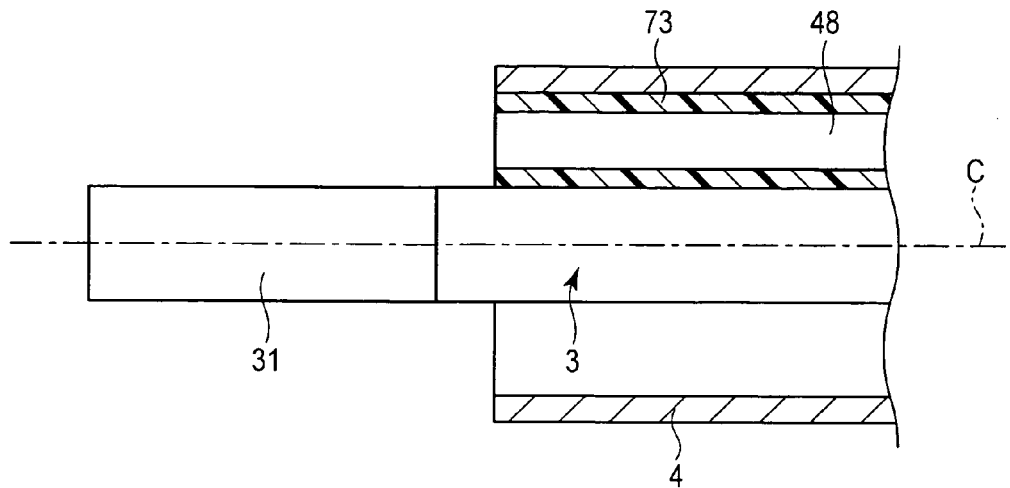
FIG. 14 is a schematic sectional view showing a state in which the ultrasonic probe is inserted through a sheath according to a second modification of the first embodiment.

According to the first embodiment, the water supply path 48 is defined by the outer peripheral portion of the ultrasonic probe 3 and the inner peripheral portion of the sheath 4. However, the present invention is not limited thereto. For example, as a second modification, a tube 73 extending along the longitudinal axis C between the ultrasonic probe 3 and the sheath 4 may be provided, as shown in FIG. 14. In this case, the water supply path 48 is formed inside the tube 73. A distal end of the tube 73 extends to substantially the same position as the distal end of the sheath 4 in the directions parallel to the longitudinal axis C. A proximal end of the tube 73 is connected to the water supply tube 51. Thus, water is supplied to, for example, living tissue from the distal end of the tube 73 (the clearance between the distal end of the sheath 4 and the ultrasonic probe 3) through the inside of the water supply tube 51 and the water supply path 48 in order.

Figure 15:
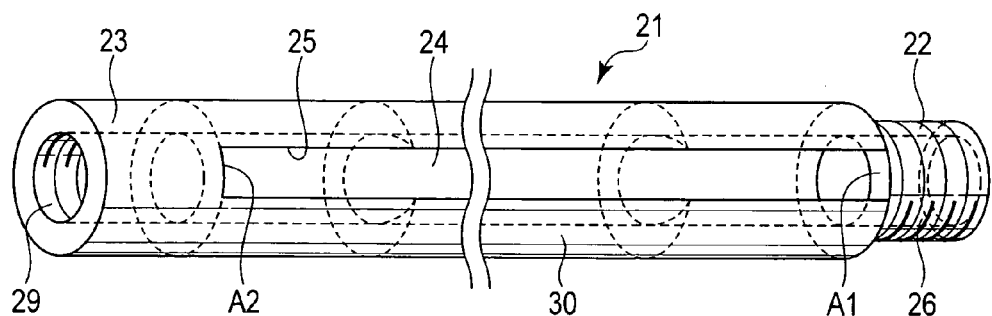
FIG. 15 is a schematic perspective view showing the probe body of the ultrasonic probe according to a third modification of the first embodiment.

According to the first embodiment, the proximal groove 27 is provided in the proximal connection portion 22 of the probe body 21, and the distal groove 28 is provided in the distal connection portion 23. However, the present invention is not limited thereto. For example, as a third modification, the proximal connection portion 22 and the distal connection portion 23 of the probe body 21 may be cylindrically shaped, as shown in FIG. 15. In this modification, the external thread 26 is formed in the outer peripheral portion 30 of the proximal connection portion 22. The internal thread 29 is formed in the inner peripheral portion of the distal connection portion 23. In the probe body 21, the groove portion 24 is defined by the groove defining surface 25. When the horn 15 and the cylindrical portion 31 are coupled to the probe body 21, the groove portion 24 is defined by the groove defining surface 25 along the longitudinal axis C from the first anti-node position A1 of the ultrasonic vibrations to the second anti-node position A2 of the ultrasonic vibrations different from the first anti-node position A1.

As described above, according to the third modification, it is only necessary that the probe body 21 is attached to the distal direction side of the horn 15, and that the cylindrical portion 31 is coupled to the distal direction side of the probe body 21. When the horn 15 and the cylindrical portion 31 are coupled to the probe body 21, the groove portion 24 has only to be defined by the groove defining surface 25 along the longitudinal axis C from the first anti-node position A1 of the ultrasonic vibrations to the second anti-node position A2 of the ultrasonic vibrations different from the first anti-node position A1.

Figure 16:
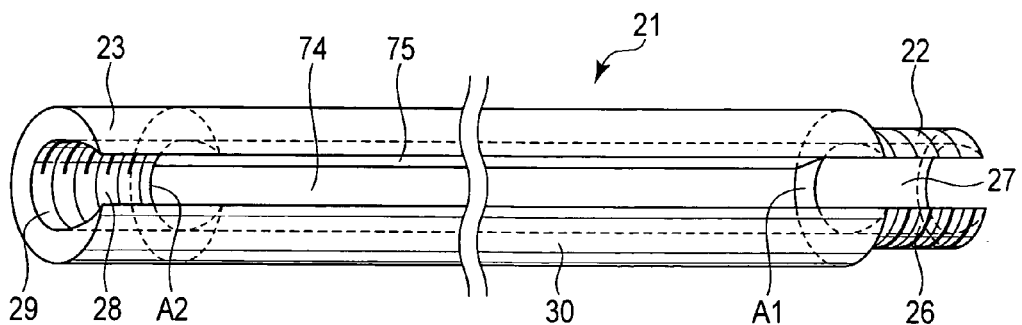
FIG. 16 is a schematic perspective view showing the probe body of the ultrasonic probe according to a fourth modification of the first embodiment.

According to the first embodiment, the groove portion 24 which is recessed from the first perpendicular direction, which is perpendicular to the longitudinal axis C, toward the second perpendicular direction is formed in the probe body 21. However, the present invention is not limited thereto. For example, as a fourth modification, a hole 74 passing through the probe body 21 from the first perpendicular direction toward the second perpendicular direction may be defined in the probe body 21 by a hole defining surface 75, as shown in FIG. 16 and FIG. 17. When the horn 15 and the cylindrical portion 31 are coupled to the probe body 21, the hole 74 is defined by the hole defining surface 75 along the longitudinal axis C from the first anti-node position A1 of the ultrasonic vibrations to the second anti-node position A2 of the ultrasonic vibrations different from the first anti-node position A1. A first-perpendicular-direction-side end and a second-perpendicular-direction-side end of the hole defining surface 75 are continuous with the outer peripheral portion 30 of the probe body 21. In this configuration, the sectional shape of the vibration transmitting portion 20 perpendicular to the longitudinal axis C changes at the first anti-node position A1 from the cylindrical shape, which is point-symmetrical about the longitudinal axis C, to a shape which is not point-symmetrical about the longitudinal axis C. Similarly, the sectional shape of the vibration transmitting portion 20 perpendicular to the longitudinal axis C changes at the second anti-node position A2 from the shape, which is not point-symmetrical about the longitudinal axis C, to the cylindrical shape, which is point-symmetrical about the longitudinal axis C.

As described above, according to the fourth modification, it is only necessary that the probe body 21 includes a void defining surface (25, 75) which defines, in the probe body, a void (24, 74) extending from the first perpendicular direction, which is perpendicular to the longitudinal axis C, toward the second perpendicular direction. The void (24, 74) has only to be defined by the void defining surface (25, 75) along the longitudinal axis C from the first anti-node position A1 of the ultrasonic vibrations to the second anti-node position A2 of the ultrasonic vibrations different from the first anti-node position A1 when the horn 15 and the cylindrical portion 31 are coupled to the probe body 21. At least the first-perpendicular-direction-side end of the void defining surface (25, 75) has only to be continuous with the outer peripheral portion 30 of the probe body 21.

Moreover, for example, as a fifth modification, a hydrophilic coating 76 may be provided on the distal face that constitutes the distal end of the ultrasonic probe 3, as shown in FIG. 18. In this modification, the entire distal face of the ultrasonic probe 3 is coated with the hydrophilic coating 76.

When the living tissue is shattered by the cavitation, pressure periodically varies in the vicinity of the distal face in response to the ultrasonic vibrations of the ultrasonic probe 3, and small air bubbles (cavities) are thereby generated in a liquid supplied to the vicinity of the treatment position of the living tissue. The generated air bubbles disappear because of force that acts when the pressure in the vicinity of the distal face increases (compression). An inelastic living tissue such as a hepatic cell is shattered and emulsified by impact energy when the air bubbles disappear.

Therefore, in order to more efficiently shatter the living tissue by cavitation, it is necessary that a proper amount of the liquid is present between the distal face of the ultrasonic probe 3 and the living tissue, and that the liquid supplied from the water supply unit 53 uniformly adheres to the distal face.

When no hydrophilic coating 76 is provided as in the first embodiment, the liquid may locally adhere to the distal face because of, for example, surface tension, and the liquid does not uniformly adhere to the distal face. Thus, the treatment efficiency when the living tissue is shattered by the cavitation decreases in a part of the distal face to which no liquid adheres.

In contrast, according to the present embodiment, the entire distal face of the ultrasonic probe 3 is coated with the hydrophilic coating 76. Thus, as shown in FIG. 19, a liquid L supplied from the water supply unit 53 uniformly adheres to the entire distal face, and a uniform layer is formed by the liquid L. Accordingly, the living tissue can be more efficiently shattered by the cavitation by using the entire distal face.

(Second Embodiment)

A second embodiment of the present invention is described with reference to FIG. 20 and FIG. 21. In the second embodiment, the configuration according to the first embodiment is modified as described below. The same parts as those according to the first embodiment are provided with the same reference marks and are not described.

FIG. 20 is a diagram showing the configuration of an ultrasonic probe 3 according to the present embodiment. FIG. 21 is a diagram showing the configuration of a probe body 21 according to the present embodiment. As shown in FIG. 20 and FIG. 21, the ultrasonic probe 3 includes the probe body 21 and a tube 41, as in the first embodiment. However, the ultrasonic probe 3 does not include a cylindrical portion 31. Therefore, the probe body 21 does not include a distal connection portion 23, and a proximal connection portion 22 is only formed integrally with the probe body 21.

As in the first embodiment, the probe body 21 is attached to a horn 15 via the proximal connection portion 22. When the probe body 21 is attached to the horn 15, the distal end of the horn 15 (the proximal end of the groove defining surface 25) is at the first anti-node position A1 of the ultrasonic vibrations. The distal end of the probe body 21 (the distal end of the groove defining surface 25) is at the second anti-node position A2 of the ultrasonic vibrations different from the first anti-node position A1. A groove portion 24 extends to the distal end of the probe body 21. Therefore, when the probe body 21 is attached to the horn 15, the groove portion 24 is defined by the groove defining surface 25 from the first anti-node position A1 to the second anti-node position A2 along the longitudinal axis C. In this configuration, the sectional shape of the vibration transmitting portion 20 perpendicular to the longitudinal axis C changes at the first anti-node position A1 from the cylindrical shape, which is point-symmetrical about the longitudinal axis C, to the recessed shape which is not point-symmetrical about the longitudinal axis C.

In the ultrasonic probe 3, the distal end of the probe body 21 is at the distal end of the ultrasonic probe 3. Cavitation is caused by the transmission of the ultrasonic vibrations to the distal end of the probe body 21 (ultrasonic probe 3) accompanied by the water supply from a water supply unit 53. As the distal end of the probe body 21 (ultrasonic probe 3) is at the second anti-node position A2 of the ultrasonic vibrations, cavitation is more efficiently caused by the transmission of the ultrasonic vibrations to the distal end of the probe body 21.

As in the first embodiment, the proximal end of the tube 41 is connected to the horn 15 at the node position (second node position) B2 located to the proximal direction side of the first anti-node position A1. The distal end of the tube 41 extends through the groove portion 24 up to the distal end of the probe body 21.

In the present embodiment, the tube 41 is fixed to the probe body 21. The tube 41 is fixed to the probe body 21 at a node position different from the node position B2. The tube 41 is fixed to the probe body 21 in the same manner as the first embodiment.

Accordingly, the ultrasonic probe 3 having the configuration described above provides the following advantageous effects in addition to the advantageous effects similar to those according to the first embodiment. That is, in the ultrasonic probe 3, the probe body 21, in which the groove portion 24 formed, accounts for a whole dimension of the ultrasonic probe 3 along the longitudinal axis C. The probe body 21 provided with the groove portion 24 is formed in a shorter time and at a lower cost than the perforation of a columnar member. The cylindrical portion 31 that needs to be perforated is not provided in the ultrasonic probe 3. Thus, perforation is not needed. Consequently, the ultrasonic probe 3 can be more efficiently manufactured at low cost.

(Modifications of Second Embodiment)

Figure 22:
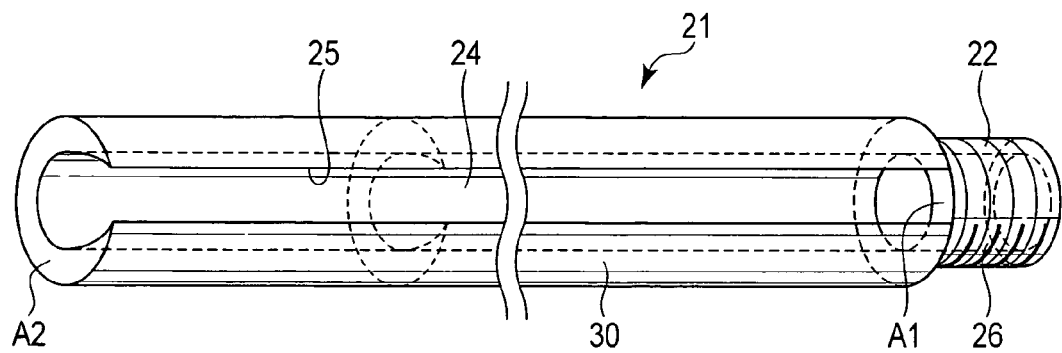
FIG. 22 is a schematic perspective view showing the probe body of the ultrasonic probe according to a first modification of the second embodiment.

According to the second embodiment, a proximal groove 27 is provided in the proximal connection portion 22 of the probe body 21. However, the present invention is not limited thereto. For example, as a first modification, the proximal connection portion 22 of the probe body 21 may be cylindrically shaped, as shown in FIG. 22. In this modification, an external thread 26 is formed in an outer peripheral portion 30 of the proximal connection portion 22. In the probe body 21, the groove portion 24 is defined by the groove defining surface 25. When the horn 15 is coupled to the probe body 21, the groove portion 24 is defined by the groove defining surface 25 along the longitudinal axis C from the first anti-node position A1 of the ultrasonic vibrations to the second anti-node position A2 of the ultrasonic vibrations which is located at the distal end of the probe body 21.

As described above, according to the first modification, it is only necessary that the probe body 21 is attached to the distal direction side of the horn 15. When the horn 15 is coupled to the probe body 21, the groove portion 24 has only to be defined by the groove defining surface 25 along the longitudinal axis C from the first anti-node position A1 of the ultrasonic vibrations to the second anti-node position A2 of the ultrasonic vibrations which is located at the distal end of the probe body 21.

Figure 23:
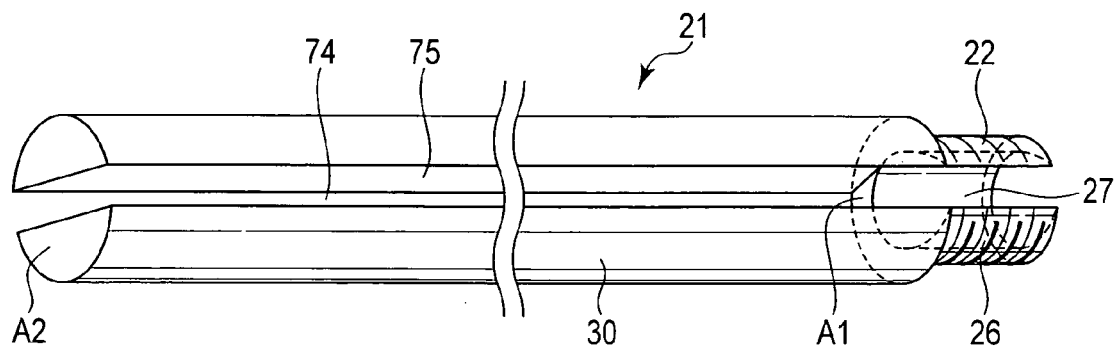
FIG. 23 is a schematic perspective view showing the probe body of the ultrasonic probe according to a second modification of the second embodiment.

According to the second embodiment, the groove portion 24 which is recessed from the first perpendicular direction, which is perpendicular to the longitudinal axis C, toward the second perpendicular direction is formed in the probe body 21. However, the present invention is not limited thereto. For example, as a second modification, a hole 74 passing through the probe body 21 from the first perpendicular direction to the second perpendicular direction may be defined in the probe body 21 by a hole defining surface 75, as shown in FIG. 23. When the horn 15 is coupled to the probe body 21, the hole 74 is defined by the hole defining surface 75 along the longitudinal axis C from the first anti-node position A1 of the ultrasonic vibrations to the second anti-node position A2 of the ultrasonic vibrations which is located at the distal end of the probe body 21. The first-perpendicular-direction-side end and the second-perpendicular-direction-side end of the hole defining surface 75 are continuous with the outer peripheral portion 30 of the probe body 21. In this configuration, the sectional shape of the vibration transmitting portion 20 perpendicular to the longitudinal axis C changes at the first anti-node position A1 from the cylindrical shape, which is point-symmetrical about the longitudinal axis C, to the shape which is not point-symmetrical about the longitudinal axis C.

As described above, according to the second modification, it is only necessary that the probe body 21 includes a void defining surface (25, 75) which defines, in the probe body, a void (24, 74) extending from the first perpendicular direction, which is perpendicular to the longitudinal axis C, toward the second perpendicular direction. The void (24, 74) has only to be defined by the void defining surface (25, 75) along the longitudinal axis C from the first anti-node position A1 of the ultrasonic vibrations to the second anti-node position A2 of the ultrasonic vibrations which is located at the distal end of the probe body 21 when the horn 15 is coupled to the probe body 21. At least the first-perpendicular-direction-side end of the void defining surface (25, 75) has only to be continuous with the outer peripheral portion 30 of the probe body 21.

In the second embodiment as well, a hydrophilic coating 76 is preferably provided in the entire distal face of the ultrasonic probe 3 as in the fifth modification of the first embodiment. Thus, the liquid supplied from the water supply unit 53 uniformly adheres to the entire distal face. Accordingly, the living tissue can be more efficiently shattered by the cavitation by using the entire distal face of the ultrasonic probe 3.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe configured to receive and transmit ultrasonic vibrations, comprising:
   a probe body having a distal portion and a proximal portion;
   a groove defining surface that defines a groove on an outer peripheral portion of the probe body; and
   a cylindrical portion that is coupled to a distal end of the probe body;
   wherein:
   the probe body has a longitudinal axis that extends from the distal portion to the proximal portion;
   the probe body is configured to:
   transmit the ultrasonic vibrations from the proximal portion to the distal portion; and
   vibrate such that a first anti-node position and a second anti-node position are located at the probe body when the probe body transmits the ultrasonic vibrations;
   the second anti-node position is different from the first anti-node position;
   the groove extends from the first anti-node position to the second anti-node position along the longitudinal axis;
   a sectional shape of the probe body perpendicular to the longitudinal axis changes at a proximal end of the groove;
   an inside of the cylindrical portion is in communication with the groove; and
   the cylindrical portion is configured to transmit the ultrasonic vibrations to a distal end of the cylindrical portion when the ultrasonic vibrations are transmitted through the probe body.

2. The ultrasonic probe according to claim 1, further comprising:
   a tube extending through the groove along the longitudinal axis,
   wherein the cylindrical portion includes a path defining surface which defines a suction path communicating with an inside of the tube, a distal end of the tube being connected to the path defining surface.

3. The ultrasonic probe according to claim 2, wherein the probe body and the cylindrical portion are configured to vibrate so that one node position, which is distal to the second anti-node position, is located at a position where the distal end of the tube is connected to the path defining surface when the probe body transmits the ultrasonic vibrations.

4. The ultrasonic probe according to claim 3, wherein:
   the probe body and the cylindrical portion are configured to vibrate so that the second anti-node position is located at a proximal end of the cylindrical portion corresponding to the distal end of the probe body and so that the one node position is located at an intermediate position between the proximal end of the cylindrical portion and the distal end of the cylindrical portion when the probe body transmits the ultrasonic vibrations,
   the cylindrical portion includes a hole defining surface which defines an insertion hole through which the tube is inserted, the hole defining surface being provided along the longitudinal axis from the proximal end of the cylindrical portion to the intermediate position of the cylindrical portion,
   the probe body and the cylindrical portion are configured to vibrate so that a third anti-node position, which is different from the first anti-node position and the second anti-node positions, is located at the distal end of the cylindrical portion,
   the path defining surface is provided along the longitudinal axis from the intermediate position of the cylindrical portion to the distal end of the cylindrical portion, and
   a sectional area of the suction path perpendicular to the longitudinal axis is less than that of the insertion hole.

5. The ultrasonic probe according to claim 1, further comprising a hydrophilic coating configured to coat a distal face of the ultrasonic probe.

6. The ultrasonic probe according to claim 1, wherein the longitudinal axis of the probe body passes through the groove.

7. The ultrasonic probe according to claim 1, wherein the ultrasonic probe is connected to a vibrator unit, which is configured to generate the ultrasonic vibrations, such that a space portion, disposed within the vibrator unit, communicates with the groove.

8. The ultrasonic probe according to claim 7, wherein the space portion of the vibrator unit communicates with a suction unit, which is configured to suction a living tissue through a suction tube connected to the vibrator unit.

* * * * *